US009463278B2

(12) United States Patent
MacDonald et al.

(10) Patent No.: US 9,463,278 B2
(45) Date of Patent: Oct. 11, 2016

(54) RESETTABLE DRIVE MECHANISM FOR A DRUG DELIVERY DEVICE WITH GUIDE TRACK AND BLOCKING MEANS

(75) Inventors: Catherine Anne MacDonald, Ashby-de-la-Zouch (GB); Robert Veasey, Leamington Spa (GB); Christopher Jones, Tewkesbury (GB); Garen Kouyoumjian, Leamington Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1231 days.

(21) Appl. No.: 13/395,701
(22) PCT Filed: Sep. 29, 2010
(86) PCT No.: PCT/EP2010/064401
§ 371 (c)(1),
(2), (4) Date: Jul. 27, 2012
(87) PCT Pub. No.: WO2011/039210
PCT Pub. Date: Apr. 7, 2011

(65) Prior Publication Data
US 2012/0283653 A1 Nov. 8, 2012

(30) Foreign Application Priority Data
Sep. 30, 2009 (EP) .................................... 09171743

(51) Int. Cl.
*A61M 5/24* (2006.01)
*A61M 5/31* (2006.01)
*A61M 5/315* (2006.01)

(52) U.S. Cl.
CPC ............. *A61M 5/24* (2013.01); *A61M 5/3146* (2013.01); *A61M 5/3156* (2013.01);
(Continued)

(58) Field of Classification Search
CPC ...... A61M 5/20; A61M 5/315; A61M 5/286; A61M 5/282; A61M 5/2425; A61M 5/2429; A61M 5/31586
See application file for complete search history.

(56) References Cited
U.S. PATENT DOCUMENTS
3,790,048 A * 2/1974 Luciano ............ A61M 5/31553 222/390
(Continued)

FOREIGN PATENT DOCUMENTS
EP 0611035 A1 8/1994
EP 0 688 571 A1 * 6/1995
(Continued)

OTHER PUBLICATIONS
Form PCT/IB/326, Notification Concerning Transmittal of International Preliminary Report on Patentability.
(Continued)

*Primary Examiner* — Kami A Bosworth
*Assistant Examiner* — Matthew A Engel
(74) *Attorney, Agent, or Firm* — McDonnell Boehnen Hulbert & Berghoff LLP (57) ABSTRACT

A resettable drive mechanism for a drug delivery device (1) comprises a piston rod assembly (32) and an interaction member (23). The piston rod assembly (32) comprises a guide track (18) running along the piston rod assembly (32), the guide track (18) comprising at least one delivery section (18A) and at least one reset section (18B). The reset section (18B) is arranged to continue the delivery section (18A). The delivery section (18A) comprises at least one blocking means (19). The interaction member (23) is configured to cooperate with the guide track (18). For delivering a dose of a drug (24), the piston rod assembly (32) is axially displaceable in a dose delivery direction away from an axial starting position, the interaction member (23) cooperating with the delivery section (18A) and the blocking means (19) passing the interaction member (23) when the piston rod assembly (32) is displaced in the dose delivery direction. Axial displacement of the piston rod assembly (32) towards the axial starting position is prevented by mechanical interaction of the blocking means (19) and the interaction member (23) when the interaction member (23) cooperates with the delivery section (18A). For resetting the drug delivery device (1), the interaction member (23) is configured to cooperate with the reset section (18B), the piston rod assembly (32) being axially displaced towards the axial starting position, the blocking means (19) being offset from the interaction member (23) and passing the axial position of the interaction member (23) when the piston rod assembly (32) is axially displaced towards the axial starting position. Also, a piston rod assembly (32) is proposed.

16 Claims, 6 Drawing Sheets

(52) U.S. Cl.
CPC ...... *A61M 5/3158* (2013.01); *A61M 5/31555* (2013.01); *A61M 5/31556* (2013.01); *A61M 5/31543* (2013.01); *A61M 2005/2407* (2013.01); *A61M 2005/2488* (2013.01); *A61M 2005/2492* (2013.01)

(56) References Cited

U.S. PATENT DOCUMENTS

| | | | | |
|---|---|---|---|---|
| 4,581,022 A * | 4/1986 | Leonard | A61M 5/31581 | 222/391 |
| 4,710,178 A * | 12/1987 | Henri | A61M 5/31581 | 401/181 |
| 4,973,318 A * | 11/1990 | Holm | A61M 5/24 | 604/208 |
| 5,112,317 A * | 5/1992 | Michel | A61M 5/24 | 222/386 |
| 5,279,585 A * | 1/1994 | Balkwill | A61M 5/3158 | 222/309 |
| 5,545,147 A * | 8/1996 | Harris | A61M 5/31551 | 604/208 |
| 5,643,214 A * | 7/1997 | Marshall | A61M 5/2033 | 604/131 |
| 5,713,857 A * | 2/1998 | Grimard | A61M 5/31596 | 604/218 |
| 5,851,197 A * | 12/1998 | Marano | A61M 5/158 | 604/131 |
| 6,068,614 A * | 5/2000 | Kimber | A61M 5/178 | 264/478 |
| 6,599,272 B1 * | 7/2003 | Hjertman | A61M 5/315 | 604/197 |
| 7,094,221 B2 * | 8/2006 | Veasey | A61M 5/31551 | 604/187 |
| 7,241,278 B2 * | 7/2007 | Moller | A61M 5/24 | 604/211 |
| 7,427,275 B2 * | 9/2008 | DeRuntz | A61M 5/31551 | 604/187 |
| 7,481,977 B2 * | 1/2009 | Percival | B01L 3/5025 | 210/324 |
| 7,850,662 B2 * | 12/2010 | Veasey | A61M 5/31546 | 604/207 |
| 7,918,833 B2 * | 4/2011 | Veasey | A61M 5/31546 | 604/209 |
| 7,935,088 B2 * | 5/2011 | Veasey | A61M 5/31546 | 604/207 |
| 7,985,201 B2 * | 7/2011 | Langley | A61M 5/20 | 604/131 |
| 7,993,301 B2 * | 8/2011 | Boyd | A61M 5/31555 | 604/211 |
| 8,257,319 B2 * | 9/2012 | Plumptre | A61M 5/31525 | 604/211 |
| 9,108,031 B2 * | 8/2015 | Brandenburger | A61J 1/2096 | |
| 2003/0105430 A1 * | 6/2003 | Lavi | A61M 5/2033 | 604/136 |
| 2004/0210199 A1 * | 10/2004 | Atterbury | A61M 5/31566 | 604/224 |
| 2004/0249348 A1 * | 12/2004 | Wimpenny | A61M 5/3158 | 604/207 |
| 2004/0260247 A1 * | 12/2004 | Veasey | A61M 5/31551 | 604/207 |
| 2005/0033244 A1 * | 2/2005 | Veasey | A61M 5/31546 | 604/211 |
| 2006/0264839 A1 * | 11/2006 | Veasey | A61M 5/31546 | 604/209 |
| 2008/0027397 A1 * | 1/2008 | DeRuntz | A61M 5/31551 | 604/220 |
| 2008/0262436 A1 * | 10/2008 | Olson | A61M 5/2033 | 604/198 |
| 2009/0198193 A1 * | 8/2009 | Veasey | A61M 5/31546 | 604/207 |
| 2009/0264828 A1 * | 10/2009 | Dette | A61M 5/31533 | 604/189 |
| 2010/0094205 A1 * | 4/2010 | Boyd | A61M 5/31595 | 604/68 |
| 2010/0094206 A1 * | 4/2010 | Boyd | A61M 5/31555 | 604/68 |
| 2010/0094207 A1 * | 4/2010 | Boyd | A61M 5/31555 | 604/68 |
| 2010/0094253 A1 * | 4/2010 | Boyd | A61M 5/31555 | 604/506 |
| 2010/0137792 A1 * | 6/2010 | Boyd | A61M 5/31555 | 604/68 |
| 2010/0324494 A1 * | 12/2010 | Plumptre | A61M 5/31551 | 604/207 |
| 2010/0324496 A1 * | 12/2010 | Plumptre | A61M 5/24 | 604/207 |
| 2010/0324497 A1 * | 12/2010 | Plumptre | A61M 5/24 | 604/207 |
| 2010/0324527 A1 * | 12/2010 | Plumptre | A61M 5/31536 | 604/500 |
| 2010/0331788 A1 * | 12/2010 | Plumptre | A61M 5/31543 | 604/207 |
| 2010/0331790 A1 * | 12/2010 | Plumptre | A61M 5/31511 | 604/207 |
| 2010/0331791 A1 * | 12/2010 | Plumptre | A61M 5/31551 | 604/207 |
| 2010/0331792 A1 * | 12/2010 | Plumptre | A61M 5/31525 | 604/207 |
| 2010/0331806 A1 * | 12/2010 | Plumptre | A61M 5/31543 | 604/500 |
| 2011/0152784 A1 * | 6/2011 | Veasey | A61M 5/31546 | 604/207 |
| 2012/0010575 A1 * | 1/2012 | Jones | A61M 5/31555 | 604/211 |
| 2012/0022462 A1 * | 1/2012 | Plumptre | A61M 5/3129 | 604/197 |
| 2012/0046643 A1 * | 2/2012 | Plumptre | A61M 5/31551 | 604/506 |
| 2012/0089098 A1 * | 4/2012 | Boyd | A61M 5/24 | 604/189 |
| 2012/0089100 A1 * | 4/2012 | Veasey | A61M 5/31546 | 604/209 |
| 2012/0283649 A1 * | 11/2012 | Veasey | A61M 5/31535 | 604/208 |
| 2012/0283651 A1 * | 11/2012 | Veasey | A61M 5/31543 | 604/210 |
| 2012/0283652 A1 * | 11/2012 | MacDonald | A61M 5/24 | 604/211 |
| 2012/0283653 A1 * | 11/2012 | MacDonald | A61M 5/24 | 604/211 |
| 2012/0283654 A1 * | 11/2012 | MacDonald | A61M 5/24 | 604/211 |
| 2012/0283658 A1 * | 11/2012 | Plumptre | A61M 5/24 | 604/211 |
| 2012/0283661 A1 * | 11/2012 | Jugl | A61M 5/31551 | 604/224 |
| 2012/0283662 A1 * | 11/2012 | MacDonald | A61M 5/24 | 604/236 |
| 2013/0030409 A1 * | 1/2013 | MacDonald | A61M 5/24 | 604/506 |
| 2014/0316347 A1 * | 10/2014 | Veasey | A61M 5/31546 | 604/211 |

FOREIGN PATENT DOCUMENTS

EP          0688571 A1     12/1995
JP          S61-30697       2/1986

OTHER PUBLICATIONS

Japanese Office Action for JP App. No. 2012-531378, mailed Jul. 15, 2014.

* cited by examiner

RESETTABLE DRIVE MECHANISM FOR A DRUG DELIVERY DEVICE WITH GUIDE TRACK AND BLOCKING MEANS

CROSS REFERENCE TO RELATED APPLICATIONS

The present application is a 35 U.S.C. 371 National Application of PCT/EP2010/064401 filed Sep. 29, 2010, which claims priority to European Patent Application No. 09171743.9, filed Sep. 30, 2009, the entire contents of which are incorporated entirely herein by reference.

This disclosure relates to an assembly for a drug delivery device and a piston rod assembly suitable to be incorporated in a drug delivery device.

In a drug delivery device, usually a cartridge that contains a drug is provided. A piston is retained in the cartridge. The piston is displaced with respect to the cartridge by a piston rod for delivering a dose of the drug.

It is an object of the present disclosure to provide a drive mechanism facilitating provision of an improved drug delivery device, for example a device with high dose accuracy. Furthermore, a piston rod assembly suitable to be integrated in an improved drug delivery device is provided.

This object may be achieved by the subject matter of the independent claims. Further features and advantageous embodiments are the subject matter of the dependent claims.

According to one aspect an assembly for a drug delivery device is provided. The assembly may be or may comprise a resettable drive mechanism. The drive mechanism may comprise a piston rod assembly. The piston rod assembly may comprise a guide track. The guide track may be a continuous guide track. The guide track may run along the piston rod assembly. The guide track may comprise at least one delivery section. The delivery section may comprise two sidewalls. The two sidewalls may form a slotted guide. The guide track may comprise at least one reset section. The reset section is expediently arranged to continue the delivery section. The delivery section may comprise at least one blocking means. The drive mechanism comprises an interaction member. The interaction member may be a flexible member. The interaction member may be configured to cooperate with the guide track. For delivering a dose of a drug the piston rod assembly may be axially displaceable in a dose delivery direction away from an axial starting position. The, preferably flexible, interaction member may cooperate with the delivery section, in particular during a dose delivery procedure. The blocking means may pass the interaction member when the piston rod assembly is displaced in the dose delivery direction. Preferably, axial displacement of the piston rod assembly towards the axial starting position is prevented by mechanical interaction of the blocking means and the interaction member when the interaction member cooperates with the delivery section. For resetting the drug delivery device, the interaction member may be configured to cooperate with the reset section of the guide track. For resetting the device, the piston rod assembly may be axially displaced towards the axial starting position. The blocking means may be offset from the interaction member, in particular when the interaction member cooperates with the reset section. The blocking means may pass the axial position of the interaction member when the piston rod assembly is axially displaced towards the axial starting position, in particular when the interaction member cooperates with the reset section.

A further aspect relates to a piston rod assembly for a drug delivery device. The piston rod assembly may comprise a continuous guide track. The guide track may run along the piston rod assembly. The guide track may comprise at least one first section. The guide track may comprise at least one second section. The first section may comprise at least one first blocking means. The first blocking means may be suitable to provide a uni-directional coupling in and/or along the first section. The first section may extend obliquely with respect to the main longitudinal axis of the piston rod assembly. The second section may be angularly offset and angularly separated from the blocking means. The second section may extend axially past the blocking means.

The first section may be the dose delivery section described previously. The second section may be the reset section described previously. The drug delivery device may be an injection device. The drug delivery device may be a pen-type device, e.g. a pen-type injector. Preferably, the drug delivery device is a device configured to dispense pre-set doses of the drug, i.e. doses whose size may not be varied by the user. The drug delivery device may provide for equally or differently sized doses of the drug. The drug may be a liquid medication, comprising for example long-acting or short-acting insulin, heparin, GLP-1 and/or growth hormones.

Preferably, the reset section is arranged to form a continuous circuit with the delivery section. Preferably, the reset section is free of a blocking means. When the interaction member cooperates with the reset section the blocking means may be angularly offset from the interaction member. Hence, due to the angular offset between the delivery section and the reset section the reset section may be passed over the interaction member without interaction of the interaction member with the blocking means arranged in the delivery section. In this way, a re-settable drug delivery device is facilitated.

Movement of the piston rod assembly during dose setting may be prevented by abutment of the blocking means and the interaction member. Thus, a drug delivery device having high dose accuracy is facilitated.

According to an embodiment, the reset section extends axially alongside the delivery section, preferably alongside the whole delivery section.

Preferably, the reset section is angularly offset with respect to the delivery section. The angular offset between reset section and delivery section may decrease in the axial direction away from the axial starting position.

For setting the piston rod assembly back to its axial starting position, the reset section mechanically cooperates with the interaction member. Thereby, the piston rod assembly may be axially displaced alongside the delivery section with an angular offset. Due to the angular offset between the reset section and the delivery section the blocking means may pass the axial position of the interaction member without mechanically interacting with the interaction member. After having displaced the piston rod assembly along the reset section, the piston rod assembly may be positioned in an axial position that the piston rod assembly had before having delivered the first dose of the drug in the cartridge i.e. the axial starting position.

Preferably, the delivery section is connected to the reset section via an angularly extending connection region of the guide track.

In particular, one end of the delivery section may be connected to one end of the reset section via one connection region of the guide track. The other end of the delivery section may be connected to the other end of the reset section or an other reset section via a further, preferably angularly extending, connection region. In this way, the reset section and the delivery section may form a continuous circuit. Thus, a resettable drug delivery device is facilitated.

Preferably, transition of the interaction member from the delivery section into the reset section may be prevented, except via the connection region, due to mechanical cooperation of the interaction member and a sidewall of the delivery section. Thus, movement of the piston rod assembly, in particular for resetting the piston rod assembly, may be prevented unless the last dose was performed.

According to an embodiment, for resetting the drive mechanism, the piston rod assembly may be rotatable. The piston rod assembly may be rotatable such that the connection region passes the interaction member and such that the interaction member is put into mechanical cooperation with the reset section. For this operation, the piston rod assembly may be rotatable in the same direction as during dose delivery.

In this way, mechanical interaction of the interaction member and the reset track is enabled and hence, provision of a resettable drug delivery device is facilitated.

Preferably, the delivery section extends obliquely with respect to a main longitudinal axis of the piston rod assembly. The reset section may extend less obliquely with respect to the main longitudinal axis of the piston rod assembly than the delivery section.

The delivery section and the interaction member may define a rotation of the piston rod assembly during delivery of each set dose. The angular offset between the two ends of the delivery section determines the total rotation angle for the rotation of the piston rod assembly from delivery of a first dose to delivery of a last dose. Preferably, the piston rod assembly is rotated by 45 degrees or less for delivering each set dose.

According to an embodiment, a section separator is arranged in the connection region. The section separator may block rotation of the piston rod assembly in that direction which would put the interaction member back into interaction with the delivery section via the connection region.

The section separator may be a step, for example. The section separator may provide a uni-directional coupling between the connection region and the interaction member. When the section separator has been passed over the interaction member, the interaction member can no longer be brought back into cooperation with the delivery section via rotation in the opposite direction. Hence, interaction of the interaction member and the delivery section may be prevented when the interaction member has been put into mechanical cooperation with the reset section for resetting the device after having delivered the last dose. For resetting the device the piston rod assembly is moved along the reset section to the axial starting position.

According to an embodiment, when the piston rod assembly has been moved back into the axial starting position, the piston rod assembly is rotatable. The piston rod assembly may be rotatable in the same direction as during dose delivery. The piston rod assembly is rotatable to put the interaction member in mechanical cooperation with the delivery section or another delivery section arranged after the reset section.

Due to rotation of the piston rod assembly the angularly extending connection region, which connects the end of the reset section with the end of another delivery section, may be brought into cooperation with the interaction member. The connection region may be passed over the interaction member such that the interaction member is put into mechanical cooperation with the delivery section. In this way, setting and delivery of a plurality of doses of a drug held in a replacement cartridge may be enabled.

Due to the section separator, in particular due to mechanical cooperation of the section separator and the interaction member, a rotation of the piston rod assembly in a direction which would put the interaction member back into mechanical cooperation with the reset section is prevented. Hence, a user-friendly and easily operated drug delivery device is achieved.

According to an embodiment, the drive mechanism comprises a drive member. The drive member may be configured to drive the axial displacement of the piston rod assembly in the dose delivery direction by mechanical interaction of a drive feature of the drive member with an interaction surface of the piston rod assembly with. For resetting the drug delivery device, the piston rod assembly may be configured to be rotatable such that the interaction surface may be angularly displaced with respect to the drive feature such that the interaction surface may pass the axial position of the drive feature with an angular offset.

The piston rod may comprise at least one set of interaction surfaces for mechanical interaction with the drive feature.

The drive member, in particular the drive feature of the drive member, may be operable to abut one of the interaction features to drive the piston rod assembly such that the piston rod assembly may be displaced in the distal direction with respect to the housing for dispensing a dose of the drug.

Due to rotation of the piston rod assembly for resetting the device, after having dispensed a last dose, mechanical interaction of the drive feature and the interaction surfaces may be prevented. In this way, axial displacement of the piston rod assembly along the reset section towards the axial starting position may be enabled and a resettable drug delivery device may be achieved.

Preferably, the drive member is secured against rotational movement with respect to the housing.

This may facilitate reliable interaction of the drive member, in particular the drive feature, with the interaction surfaces of the piston rod assembly.

According to an embodiment, the delivery section may comprise a plurality of dose sections. Two adjacent dose sections may be separated by the blocking means.

The dose sections may be disposed along the delivery section of the piston rod, one after the other. An axial extension of a dose section may correspond to the size of the delivered dose. The dose sections, in particular mechanical cooperation of the interaction member with one dose section, may define the rotation angle of the piston rod assembly during dose delivery. The blocking means may prevent rotation and axial movement of the piston rod assembly during dose setting.

According to an embodiment, the guide track is provided at an outer surface of the piston rod assembly. The interaction surface may be provided at an inner surface of the piston rod assembly.

The piston rod assembly may comprise a piston rod. The piston rod assembly may comprise a piston rod sleeve. The piston rod may be positioned concentrically inside the piston rod sleeve. The piston rod and the piston rod sleeve may be rotationally and/or axially fixed to each other or may be formed unitarily. A surface of the piston rod may form the inner surface of the piston rod assembly. The outer surface of the piston rod sleeve may form the outer surface of the piston rod assembly. In this way, a space saving drive mechanism and hence, a space saving drug delivery device is achieved.

According to a preferred embodiment, a resettable drive mechanism for a drug delivery device is provided. The drive mechanism comprises a piston rod assembly, the piston rod assembly comprising a guide track running along the piston rod assembly, the guide track comprising at least one delivery section and at least one reset section, the reset section being arranged to continue the delivery section, the delivery section comprising at least one blocking means. The drive mechanism comprises an interaction member, the interaction member being configured to cooperate with the guide track. For delivering a dose of a drug, the piston rod assembly is axially displaceable in a dose delivery direction away from an axial starting position, the interaction member cooperating with the delivery section and the blocking means passing the interaction member when the piston rod assembly is displaced in the dose delivery direction, axial displacement of the piston rod assembly towards the axial starting position being prevented by mechanical interaction of the blocking means and the interaction member when the interaction member cooperates with the delivery section. For resetting the drug delivery device, the interaction member is configured to cooperate with the reset section, the piston rod assembly being axially displaced towards the axial starting position, the blocking means being offset from the interaction member and passing the axial position of the interaction member when the piston rod assembly is axially displaced towards the axial starting position.

In this way, an easily operated and effective resettable drive mechanism is provided. The drive mechanism has a low number of components. Thus, a cost-effective drug delivery device is achieved being less prone to errors in manufacture and assembly.

According to a preferred embodiment, a piston rod assembly for a drug delivery device is provided. The piston rod assembly comprises a continuous guide track running along the piston rod assembly, the guide track comprising at least one first section and at least one second section. The first section comprises at least one first blocking means suitable to provide a uni-directional coupling along the first section. The first section extends obliquely with respect to the main longitudinal axis of the piston rod assembly. The second section is angularly offset and angularly separated from the blocking means and extends axially past the blocking means.

Of course, features from different aspects and embodiments described above may be combined with each other and with features described below.

Like elements, elements of the same kind and identically acting elements may be provided with the same reference numerals in the figures.

Figure 1A:
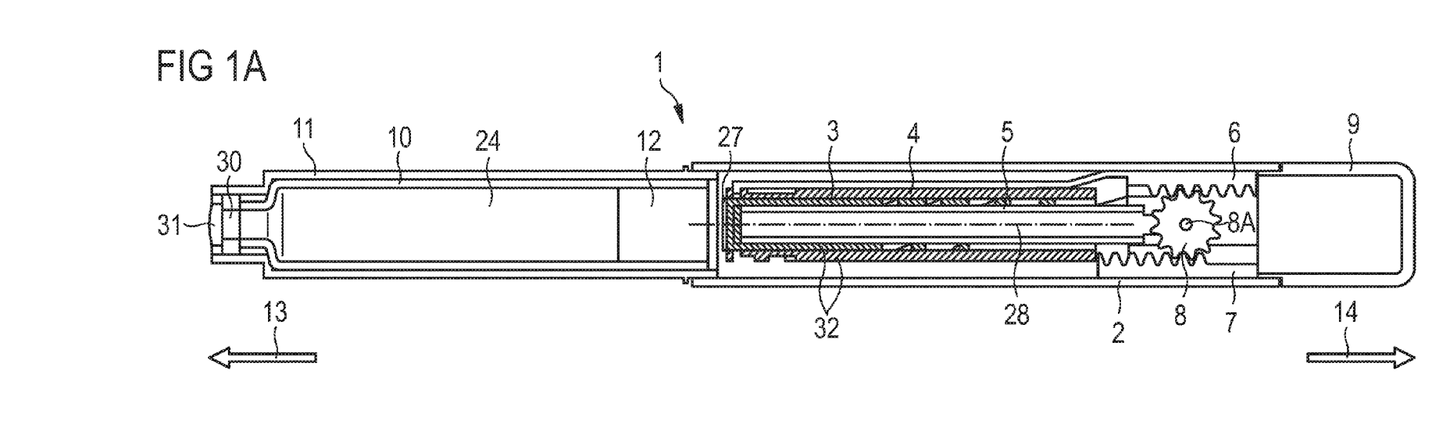
FIG. 1A and FIG. 1B schematically show a partly sectional side view of an exemplary embodiment of a drug delivery device, FIG. 2A through 2C schematically show parts of the drug delivery device of FIG. 1, FIG. 3 schematically shows a part of the drug delivery device of FIG. 2 in more detail, FIG. 4A and FIG. 4B schematically show a sectional view of the drug delivery device of FIG. 1 after setting of a priming dose, FIG. 5A and FIG. 5B schematically show a sectional view of the drug delivery device of FIG. 4 after having delivered a priming dose, FIG. 6A and FIG. 6B schematically show the drug delivery device of FIG. 1 after delivery of the last dose.
Figure 1B:
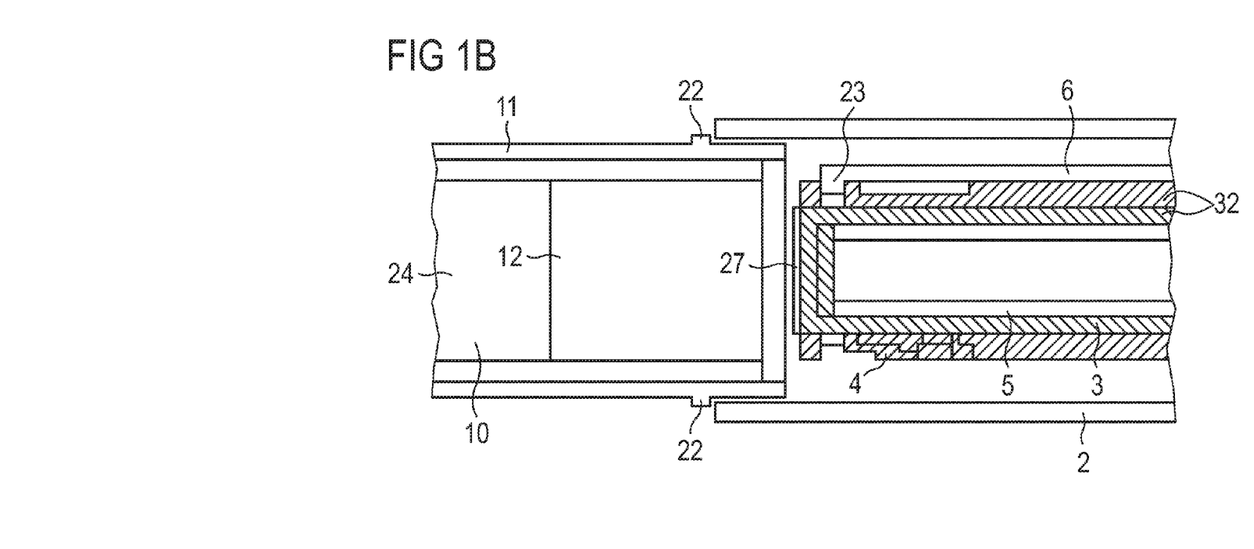

In FIG. 1 an exemplary embodiment of a drug delivery device 1 is shown. The drug delivery device 1 comprises a housing 2. The drug delivery device 1 comprises a piston rod assembly 32. The piston rod assembly 32 comprises a piston rod 3. The piston rod assembly 32 comprises a piston rod sleeve 4.

The drug delivery device 1 comprises a cartridge holder 11. The drug delivery device 1 comprises a cartridge 10. The cartridge holder 11 retains and stabilizes the cartridge 10 mechanically. The cartridge 10 may hold one of or preferably a plurality of doses of a drug 24. The drug 24 is preferably a liquid medication, comprising, for example, insulin, like short-acting or long acting-insulin, GLP-1, heparin or growth hormones. The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 10 has an outlet 30. The drug 24 can be dispensed from the cartridge 10 through the outlet 30. The outlet 30 may be covered by a membrane 31. The membrane 31 may protect the drug 24 against external influences during storage of the cartridge 10. The drug delivery device 1 comprises a piston 12. The piston 12 may be retained in the cartridge 10.

The cartridge 10 is, preferably releasably, secured in the cartridge holder 11. A cartridge 10, which is releasably secured in the cartridge holder 11 may be detached from the cartridge holder 11, thereby allowing for a replacement cartridge to be introduced into the cartridge holder 11, e.g. when all of the doses of the drug 24 that once were in the cartridge 10 have been dispensed.

The drug delivery device 1 may comprise a needle assembly (not explicitly shown), comprising for example a needle covered by a needle mount, a needle retainer and a needle seal. The needle assembly may be releasably attached to a distal end of the cartridge holder 11. The membrane 31 may be pierced by the needle assembly for dispensing a dose of the drug 24. Alternatively, the drug delivery device 1 may be a needle-free device.

The drug delivery device 1 and the housing 2 have a distal end and a proximal end. The distal end of the device 1 is indicated by arrow 13. The distal end designates the end of the drug delivery device 1 or a component thereof which is or is to be arranged closest to a dispensing end of the drug delivery device 1. The proximal end of the device 1 is indicated by arrow 14. The proximal end designates the end of the device 1 or a component thereof which is or is to be arranged furthest away from the dispensing end of the device 1.

The drug delivery device 1 may be a pen-type device, in particular a pen-type injector. The device 1 may be a disposable or a re-usable device and may be configured to dispense fixed doses of the drug 24 or variable, preferably user-settable doses of the drug 24. The drug delivery device 1 may be a manually, in particular a non-electrically, driven device.

The cartridge holder 11 is, preferably releasably, connected to the distal end of the housing 2, for example by means of a threaded connection or a snap fit connection. The position of the cartridge holder 11 with respect to the housing 2 may, for example, be determined by means of one or more stop members 22 (see FIG. 1B) arranged at a proximal end section of the cartridge holder 11. In particular, abutment of the distal end section of the housing 2 may prevent further proximal displacement of the cartridge holder 11 with respect to the housing 2.

The housing 2 is designed to enable safe and comfortable handling of the drug delivery device 1. The housing 2 may be configured to house, fix, protect or guide inner components of the drug delivery device 1, e.g. the piston rod assembly 32. Preferably, the housing 2 limits or prevents exposure of the inner components to contaminants such as liquid, dirt or dust. The housing 2 may be a unitary or a multipart component. The housing 2 may comprise a tubular or cylindrical shape, as shown in FIG. 1. Alternatively, the housing 2 may comprise a non-tubular shape.

The piston 12 is retained within the cartridge 10. The piston 12 is movable with respect to the cartridge 10. The piston 12 may seal the cartridge 10 proximally. Movement of the piston 12 in the distal direction with respect to the cartridge 10 causes drug 24 to be dispensed from the cartridge 10 through the outlet 30.

The piston rod assembly 32 may operate through the housing 2 of the drug delivery device 1. The piston rod assembly 32 is designed to transfer axial movement through the drug delivery device 1, for example for the purpose of dispensing the drug 24. In particular, the piston rod assembly 32 is designed to transfer force to the piston 12, thereby pushing the piston 12 in the distal direction with respect to the housing 2. In this way, a dose of the drug 24 is dispensed from the cartridge 10. The size of the dispensed dose is determined by the distance by which the piston 12 is displaced in the distal direction with respect to the cartridge 10.

A bearing member 27 may be arranged between the piston 12 and the piston rod assembly 32 to advance the piston 12. The bearing member 27 may be fixed to the piston rod assembly 32 or may be a separate member. The bearing member 27 may be displaced together with the piston rod assembly 32 with respect to the housing 2. The piston rod assembly 32 may be rotatable with respect to the bearing member 27. Rotational friction between the piston 12 and the piston rod assembly 32 may be minimised in this way.

The drug delivery device 1 comprises a drive mechanism. The drive mechanism is located within the housing 2 of the device 1. The piston rod assembly 32 may be part of the drive mechanism. The drive mechanism comprises a drive member 5. The drive mechanism comprises a first rack 6. The first rack 6 may be a fixed rack. The first rack 6 is secured against axial and rotational displacement with respect to the housing 2. Alternatively, the first rack 6 and the housing 2 may be unitary.

The drive mechanism comprises a second rack 7. The second rack 7 is a movable rack. The second rack 7 is configured to be moved axially, but not rotationally with respect to the first rack 6.

The drive mechanism comprises a gear 8. Gear 8 may be a toothed gear wheel, for example. Gear 8 is located between the first rack 6 and the second rack 7. Gear 8 is in engagement with the first rack 6 and the second rack 7. The gear 8 is rotatable about an axle 8A.

Figure 2A:
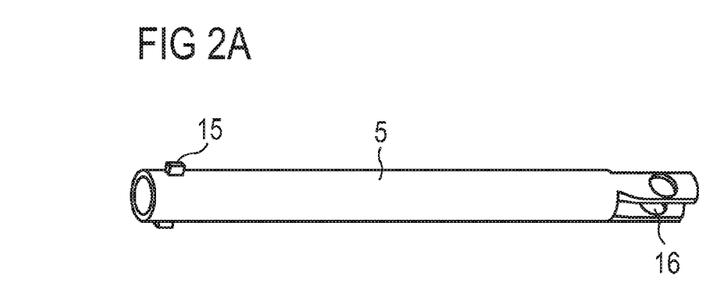

A proximal end section of the drive member 5 is connected to the axle 8A of the gear 8 (see FIG. 2A). At the proximal end section the drive member 5 comprises engaging means 16. Engaging means 16 may comprise indentations or openings, for example. Via engaging means 16 the gear 8, in particular the axle 8A, is connected to the proximal end section of the drive member 5. For example, the gear 8 may be snap-fitted to the drive member 5 by means of engaging means 16. Thus, the gear 8 is rotatable about axle 8A with respect to the drive member 5. The gear 8 is axially locked to the drive member 5.

The device 1 comprises at least one interaction member 23 (see FIG. 1B). The interaction member 23 may be a lug, for example. The interaction member 23 may be a flexible tooth. The interaction member 23 is rotationally and axially locked with respect to the housing 2. Preferably, the interaction member 23 is part of the fixed rack 6. The interaction member 23 may protrude radially inwardly. The interaction member 23 is configured to mechanically cooperate with the piston rod assembly 32 as described later on in more detail.

The drive mechanism comprises a dose member 9. The dose member 9 is movable for setting and delivering a dose. The dose member 9 is preferably rotationally locked with respect to the housing 2. The second rack 7 may be rigidly and permanently mounted to the dose member 9. Alternatively, the second rack 7 and the dose member 9 are of unitary construction. The second rack 7 and the dose member 9 are configured to be moved axially together with respect to the housing 2 and with respect to the first rack 6. Operation of the drive mechanism is described later on in connection with the description of FIGS. 4 to 6.

Figure 2B:
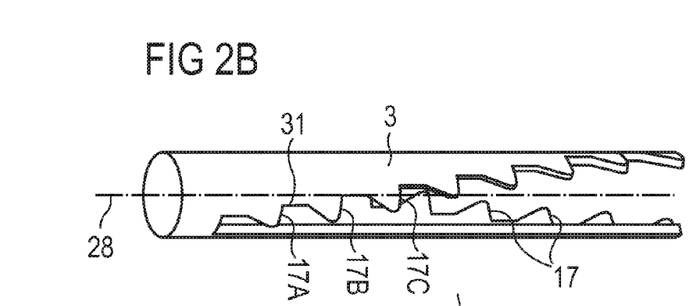
Figure 2C:
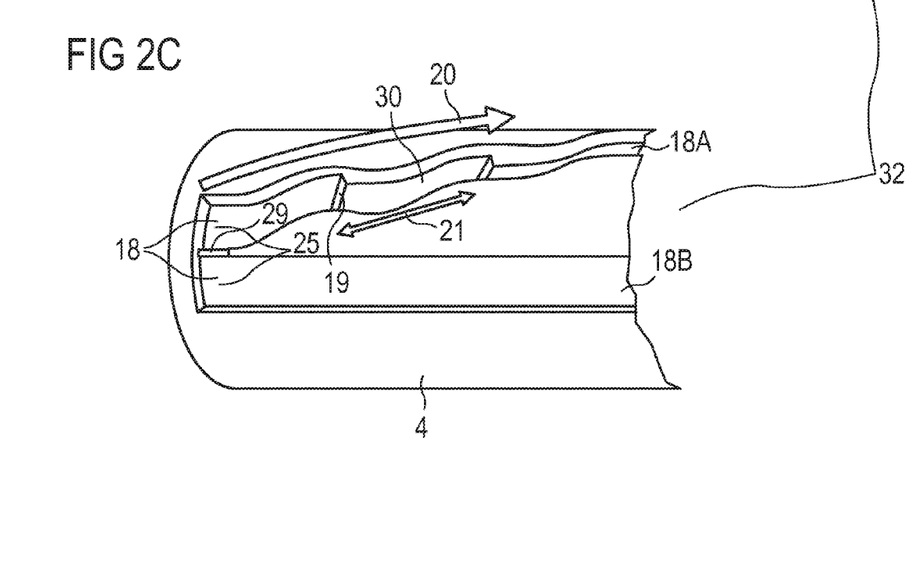
Figure 3:
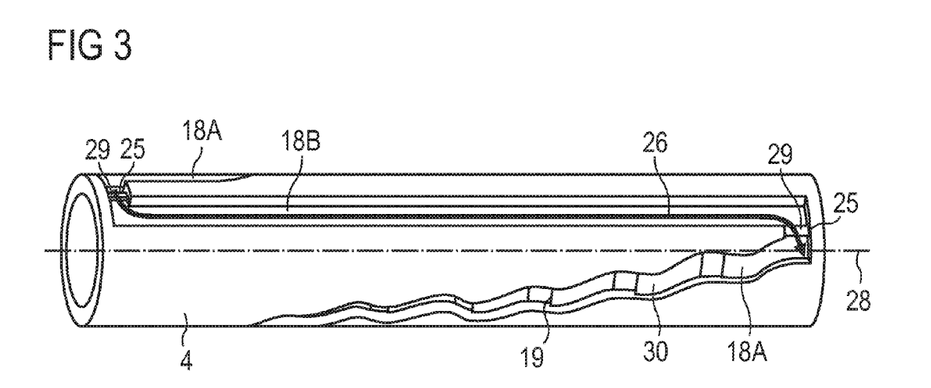

FIG. 2A through 2C schematically show parts of the drug delivery device of FIG. 1. FIG. 2A shows the drive member 5. FIG. 2B shows the piston rod 3. FIG. 2C shows a distal end section of the piston rod sleeve 4. FIG. 3 shows the piston rod sleeve 4.

The drive member 5 may comprise a rod, for example. The drive member 5 may be provided with at least one drive feature 15. In this embodiment, the drive member 5 comprises two drive features 15.

The drive feature 15 may be a lug, for example. The drive feature 15 may be positioned at a distal end region of the drive member 5. The drive feature 15 may be integrally formed with the drive member 5. Alternatively, the drive feature 15 may be connected to the drive member 5. The drive feature 15 may protrude radially from the drive member 5. If there are two drive features 15, these drive features 15 may be oppositely disposed.

The drive feature 15 is configured for mechanical interaction with the piston rod assembly 32. In particular, the drive feature 15 may act upon the piston rod assembly 32 to drive the piston rod assembly 32 such that the piston 12 is advanced in the distal direction with respect to the housing 2 for delivery of a dose. This is described later on in more detail.

The drive member 5 may be an elastically deformable member. In particular, the drive member 5 may be twistable under a setting load, but not compressible under a dispensing load.

The drive member 5 is displaced in a dose setting direction with respect to the housing 2 for setting a dose of the drug 24. The dose setting direction may be the proximal direction with respect to the housing 2. The drive member 5 is displaced in a dose delivery direction with respect to the housing 2 for delivering the set dose of the drug 24. The dose delivery direction may be the distal direction with respect to the housing 2. The drive member 5 is secured against rotational movement with respect to the housing 2.

The piston rod 3 (FIG. 2B) is positioned, preferably concentrically, inside the piston rod sleeve 4 (FIG. 2C). The piston rod 3 and the piston rod sleeve 4 are rigidly and permanently secured to each other. The piston rod 3 may be glued into the piston rod sleeve 4, for example. Alternatively, the piston rod assembly 32 may be unitary. The drive member 5 may be arranged within the piston rod assembly 32.

The piston rod assembly 32 has an inner surface. The piston rod assembly 32 has an outer surface. A surface of the piston rod 3 may form the inner surface of the piston rod assembly 32. The outer surface of the piston rod sleeve 4 may form the outer surface of the piston rod assembly 32.

The piston rod 3 comprises at least one set of interaction surfaces 17. The interaction surfaces 17 are arranged for mechanical interaction with the drive feature 15. Preferably, the piston rod 3 comprises two sets of interaction surfaces 17. Expediently, the piston rod 3 has 180 degrees rotational symmetry about its main longitudinal axis. Preferably, the drive member 5 comprises two drive features 15. One set of interaction surfaces 17 may be configured to interact with one of the drive features 15 of the drive member 5. The other set of interaction surfaces 17 may be configured to interact with the other one of the drive features 15. In particular, the drive member 5 may be configured to drive an axial displacement of the piston rod assembly 32 in the dose delivery direction by mechanical interaction of one of the interaction surfaces 17 of the piston rod 3 with the drive features 15 of the drive member 5.

The interaction surfaces 17 of one of the two sets may be arranged angularly offset from the other set of interaction surfaces 17. Within each set of interaction surfaces 17, each individual interaction surface 17A, 17B etc. may be axially offset from one another. Within each set, the interaction surfaces 17 may also be angularly offset from one another. Two adjacent interaction surfaces 17A, 17B may at least partly overlap angularly.

The interaction surfaces 17 of one set of interaction surfaces may be arranged at least partly step-like along the piston rod 3. In particular, the interaction surfaces 17 may be disposed about the main longitudinal axis 28 of the piston rod assembly 32 like steps of a spiral staircase. Thereby, one of the steps may have an overhang with respect to the adjacent step. The interaction surfaces 17 may be arranged at equidistant intervals along the piston rod 3. The distance between two adjacent interaction surfaces 17 may correspond to the size of a dose of the drug 24. In this way, provision of a fixed-dose drug delivery device, i.e. a device delivering pre-set doses of the drug 24, in particular doses whose size may not be varied by the user, may be enabled.

The angular offset of two adjacent interaction surfaces 17A, 17B may be the same as the rotation angle by which the piston rod assembly 32 is rotated when delivering the dose, which is described in connection with the description of FIGS. 4 to 6. Two adjacent interaction surfaces 17A, 17B may be connected with each other via a ramp 31. The ramp 31 may be oriented axially. The ramp 31 may run obliquely with respect to the main longitudinal axis 28 of the piston rod assembly 32. Between the ramp 31 and a preceding interaction surface a section may be arranged that runs parallel with respect to the main longitudinal axis 28 of the piston rod assembly 32. This section is followed by the ramp 31 which rises in the proximal direction with respect to the housing 2.

The piston rod sleeve 4 (FIG. 2C and FIG. 3) may be a cylindrical shape. The piston rod sleeve 4 may comprise at least one guide track 18. The guide track 18 runs along an outer surface of the piston rod sleeve 4. The guide track 18 may be a guide channel. The guide track 18 may be a slotted guide. The guide track 18 may be a continuous guide track arranged angularly around the piston rod sleeve 4 as described later on in more detail.

The guide track 18 comprises at least one delivery section 18A. The delivery section 18A comprises two sidewalls. The two sidewalls form a slotted guide. The delivery section 18A is oblique with respect to the main longitudinal axis 28 of the piston rod assembly 32. The delivery section 18A may be curved. The delivery section 18A comprises a plurality of dose sections succeeding each other. One dose section may define an oblique portion of the delivery section 18A. A dose section is indicated by arrow 21 in FIG. 2C. The respective dose section comprises a ramp 30. The ramp 30 may have an edge. The edge may define a blocking means 19. The blocking means 19 may enable a uni-directional coupling between the delivery section 18A and the interaction member 23 along the delivery section 18A which will be described later on in more detail. Two adjacent dose sections may be separated by the blocking means 19. Ramp 30 may rise in the direction of the blocking means 19 in the proximal direction.

An axial extension of a dose section may correspond to the axial distance between two corresponding interaction surfaces 17 of the piston rod 3. The dose sections may be suitable together with the interaction member 23 to define a rotation of the piston rod assembly 32, which will be described later on in more detail. In particular, the angular extension of a dose section may define the rotation angle for the rotation of the piston rod assembly 32 when the interaction member 23 interacts with that dose section. The rotation angle may correspond to the angular offset of two adjacent interaction surfaces 17A, 17B as mentioned above.

The delivery section 18A may extend in the angular direction by less than 360 degrees over its total axial extension. The angular extension of the delivery section 18A over its total axial extension may define the total rotation angle of the piston rod assembly 32 from delivery of the first dose of the drug 24 to delivery of a last available, i.e. the final, dose of the drug 24. Preferably, the delivery section 18A extends by 180 degrees or less in the angular direction.

The guide track 18 may comprise at least one reset section 18B. The reset section 18B is arranged to continue the delivery section 18A. In particular, the reset section 18B is arranged to form a continuous circuit with the delivery section 18A. The continuous circuit may run angularly around the whole piston rod assembly 32. The guide track 18 may be a closed track. In case there are at least two delivery sections 18A and at least two reset sections 18B, the delivery section 18A and the reset section 18B may be arranged alternately along the guide track 18.

The delivery section 18A may be connected to the reset section 18B via a connection region 25 (see also FIG. 3). In particular, the distal end of the reset section 18B may be connected to the distal end of the delivery section 18A via connection region 25. The proximal end of the reset section 18B may be connected either to the proximal end of the delivery section 18A or to the proximal end of an other delivery section 18A via an other connection region.

The reset section 18B extends axially alongside the delivery section 18A. The reset section 18B may be less oblique with respect to the main longitudinal axis 28 of the piston rod assembly 32 than the delivery section 18A. The reset section 18B may be free of a blocking means at the axial positions of the blocking means 19 of the delivery section 18A.

The reset section 18B is angularly offset from the delivery section 18A. The angular offset between reset section 18B and delivery section 18A may vary in the axial direction. In particular, the angular offset between reset section 18B and delivery section 18A may decrease in the axial direction towards the connection region 25 arranged between reset section 18B and delivery section 18A.

Preferably, the connection region 25 is arranged at an end of the respective section 18A, 18B. The connection region 25 may extend angularly. A section separator 29 may be arranged in the connection region 25. The section separator 29 may be a step, for example. The section separator 29 provides a non-return feature. The function of the section separator 29 is explained in connection with the description of FIGS. 4 to 6.

Via the guide track 18, in particular via the delivery section 18A and the reset section 18B, the piston rod assembly 32 may be keyed to the fixed rack 6. In particular, the piston rod assembly 32 may be keyed to the fixed rack 6 due to mechanical cooperation of the delivery section 18A and the reset section 18B with the interaction member 23. The guide track 18 may be passed along the interaction member 23 for enabling axial and rotational movement of the piston rod assembly 32 for delivering a dose of the drug 24 (see description of FIGS. 4 to 6).

Figure 4A:
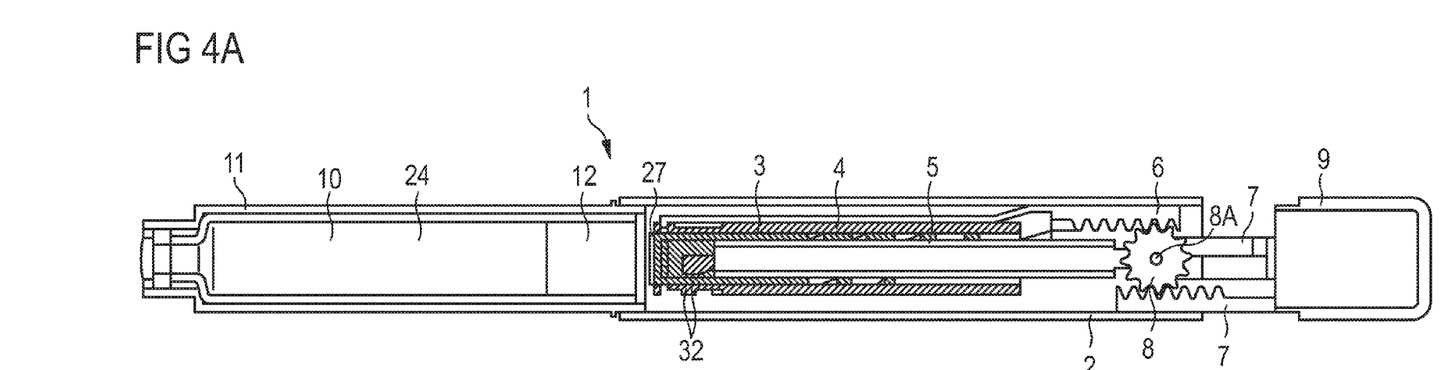
Figure 4B:
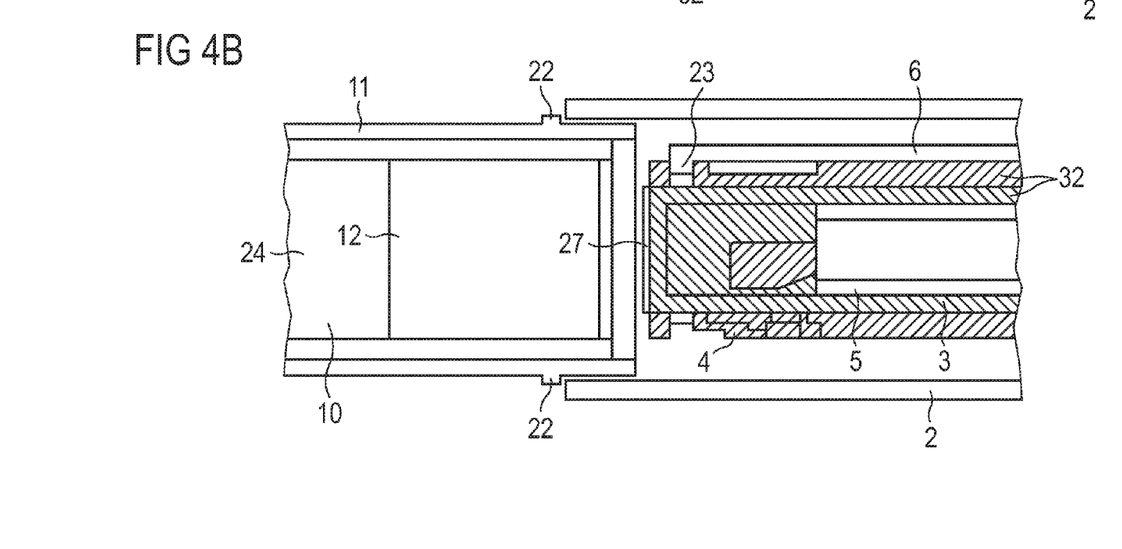

FIG. 4A and FIG. 4B schematically show a sectional view of the drug delivery device of FIG. 1 after setting of a priming dose.

Figure 5A:
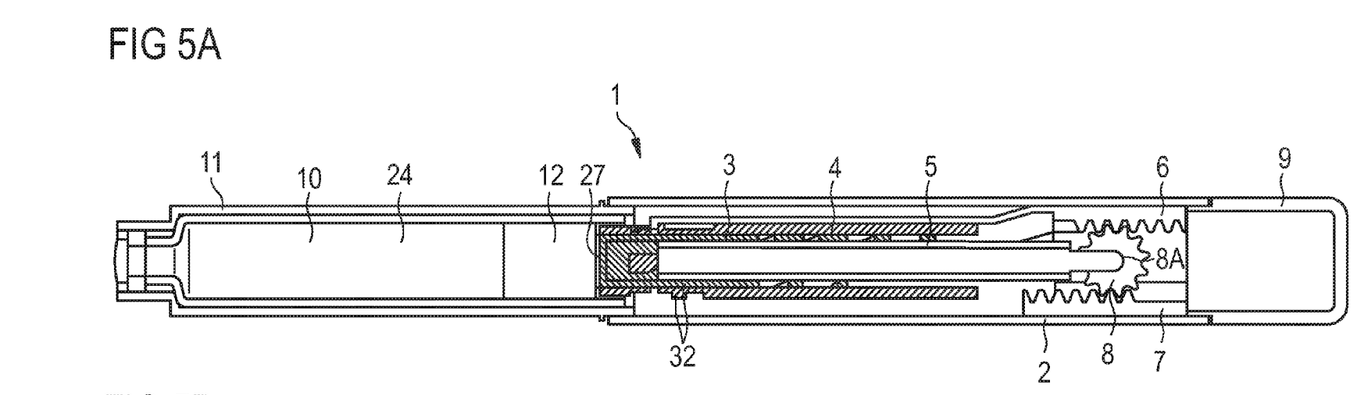
Figure 5B:
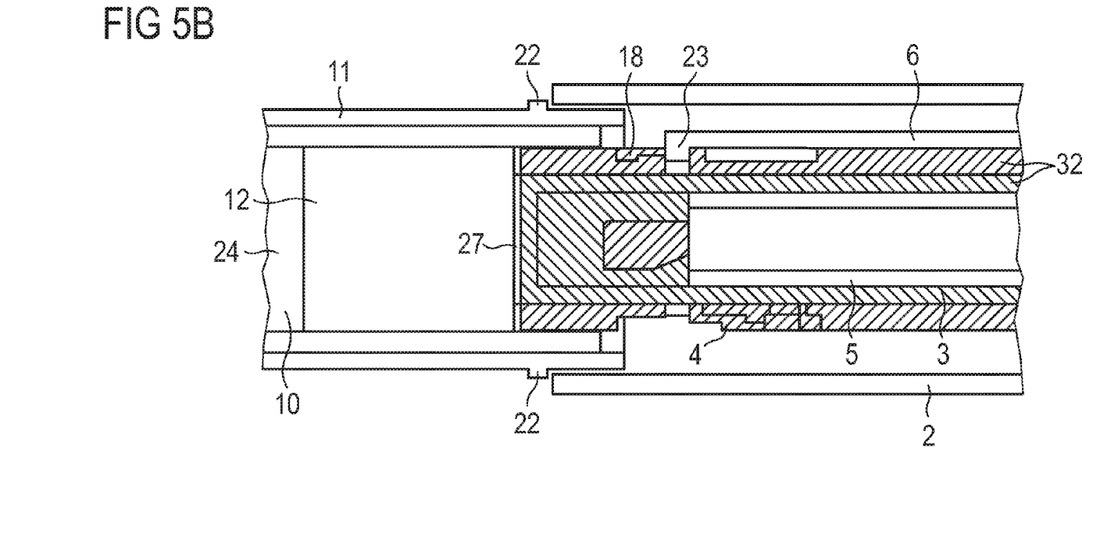

FIG. 5A and FIG. 5B schematically show a sectional view of a part of the drug delivery device of FIG. 4 after having delivered the priming dose.

In an initial state of the device 1, there may be a gap between members of the drive mechanism, e.g. the piston rod assembly 32 and the piston 12. The gap may arise from manufacturing or assembly tolerances. The size of the gap may vary. However, when delivering the drug 24, the gap between the piston rod assembly 32 and the piston 12 may reduce the dose accuracy, because the piston rod assembly 32 has to close the gap before the piston 12 is advanced and drug 24 is expelled.

Priming of the device, in particular dispensing of a priming dose, may be intended to remove the gap between the piston rod assembly 32 and the piston 12. After having removed the gap, a first dose of the drug 24 can be set and delivered to the user.

Before setting and delivering the priming dose the piston rod assembly 32 may be positioned in an axial starting position with respect to the housing 2. The piston rod assembly 32 is keyed to the housing 2 by means of the interaction member 23 and the guide track 18.

When setting and delivering a dose the interaction member 23 may be arranged to mechanically interact with the delivery section 18A. In particular, before setting the priming dose of the drug 24 held in the cartridge 10 the interaction member 23 may be positioned in the most distal dose section of the delivery section 18A of the guide track 18. The interaction member 23 may abut the blocking means 19 arranged at the distal end of the most distal dose section. After having dispensed the priming dose, the interaction member 23 may be position in the dose section succeeding the most distal dose section of the delivery section 18A.

In the following operation of the drive mechanism for setting and delivering the first dose will be described. Setting and delivering of the priming dose may occur in the same way.

In order to set the first dose, the user may pull the dose member 9 in the proximal direction with respect to the housing 2. As the dose member 9 is rotationally locked with respect to the housing 2, the dose member 9 is not rotatable for setting the dose. The second rack 7 may be proximally displaced with respect to the housing 2 by the same distance as the dose member 9.

This may cause the gear 8 to rotate about axle 8A. The gear 8 may move along the first rack 6 in the proximal direction with respect to the housing 2 a distance that is half the distance moved by the dose member 9 and second rack 7. Thereby, the drive member 5, which is connected to the gear 8, is displaced in the proximal direction with respect to the housing 2.

The piston rod assembly 32 is secured against proximal displacement with respect to the housing 2 due to mechanical interaction of the interaction member 23 and blocking means 19.

When the drive member 5 is displaced in the dose setting direction, the drive member 5 may be axially displaced from a first interaction surface 17A, which the drive member 5 abuts after having primed the device 1, towards a proximally subsequent interaction surface 17B. The distance between the first interaction surface 17A and the subsequent interaction surface 17B may correspond to the size of the dose which is to be delivered.

When the drive member 5 is displaced proximally the drive feature 15 is guided proximally along ramp 31 arranged between the first interaction surface 17A and the subsequent interaction surface 17B. The drive member 5, in particular its distal end section, may be elastically deflected in torsion about the main longitudinal axis of piston rod assembly 28 by mechanical interaction of the drive feature 15 and the ramp 31 as the proximal end of the drive member 5 is secured against rotational movement. At the end of the ramp 31 the drive feature 15 may snap over the end of the ramp so that it is in a position to be able to mechanically cooperate with the subsequent interaction surface 17B for dispensing the set dose. The drive features 15 now abut the flat section of interaction surface 17B. The snap may give the user audible and/or tactile feedback that the dose has been set (FIG. 4). When the set dose is delivered the drive feature 15 mechanically cooperates, in particular abuts, the interaction surface 17B.

To dispense the set dose, the user may push the dose member 9 in the distal direction with respect to the housing 2. Thereby, the second rack 7 is displaced in the distal direction by the same distance. This causes the gear 8 to rotate in an opposite direction about axle 8A compared to rotation of the gear 8 when setting the dose. As the gear 8 rotates, it may move together with the drive member 5 along the first rack 6 in the distal direction with respect to the housing 2 a distance that is half the distance moved by the dose member 9 and second rack 7.

Thereby, the drive feature 15 mechanically interacts with, e.g. abuts, the interaction surface 17B. Due to mechanical interaction of the drive feature 15 with the interaction surface 17B the piston rod assembly 32 is moved in the dose delivery direction, i.e. the distal direction with respect to the housing 2, away from the axial starting position. The piston rod assembly 32, is moved in the distal direction by half of the distance the dose member 9 is axially displaced with respect to the housing 2. Hence, the device 1 provides a 2:1 mechanical advantage. Different mechanical advantages can be achieved e.g. by means of a lever interacting with fixed and moving pivots rather than a gear interacting with fixed and moving rack 6, 7 as illustrated.

When the piston rod assembly 32 is distally displaced with respect to the housing 2 the most distal dose section of the delivery section 18A is passed along the interaction member 23. The axial extension of the dose section may correspond to the distance by which the piston rod assembly 32 is displaced in the distal direction with respect to the housing 2. The axial extension of the dose section may correspond to the size of the dose. The axial extension of the dose section is indicated by arrow 21 in FIG. 2C. The axial extension of one dose section may be less than or equal to the distance between the two adjacent interaction surfaces 17A, 17B.

While dispensing the first dose the interaction member 23 interacts with ramp 30 (see also arrow 20, FIG. 2C) of the most distal dose section. At the end of the ramp 30 the interaction member 23 may click over to mechanically interact with the blocking means 19 which is arranged between the most distal dose section and an adjacent dose section. Hence, after having delivered the first dose the interaction means 23 may mechanically cooperate with the blocking means 19 of the dose section that is adjacent to the most distal dose section.

When the interaction member 23, which may comprise a flexible tooth, for example, clicks over to mechanically cooperate with the blocking means 19 of the adjacent dose section an audible and/or tactile feedback may be given to indicate that the dose has been dispensed (FIG. 5). Axial displacement of the piston rod assembly 32 within the delivery section 18A back towards the axial starting position may be prevented by mechanical interaction of the blocking means 19 and the interaction member 23.

In addition to the axial displacement, the piston rod assembly 32 may be rotated during dose delivery with respect to the housing 2 due to cooperation of the interaction member 23 and the delivery section 18A. Thereby, mechanical interaction of the interaction member 23 and the delivery section 18A, in particular a sidewall of the delivery section 18A, may define the rotation of the piston rod assembly 32 with respect to the housing 2. In particular, an angle formed by the dose section and the main longitudinal axis 28 of the piston rod assembly 32 may correspond to the rotation angle of the piston rod assembly 32. The piston rod assembly 32 may be rotated by 45 degrees or less when delivering the set dose. For example, the piston rod assembly 32 is rotated by approximately 15 degrees for delivering the dose.

Due to rotation of the piston rod assembly 32 while dispensing the dose the interaction surface 17B that the drive feature 15 interacts with is rotated and slides over the drive feature 15. Accordingly, an interaction surface 17C, which is adjacent to the interaction surface 17B, is rotated from a non-interaction position into the interaction position. In particular, due to the rotational movement of the piston rod assembly 32, the interaction surface 17C may be rotated into the angular position the interaction surface 17B had before mechanically interacting with the drive feature 15 for setting and delivery of the dose. In this way, delivering of a subsequent dose of the drug 24 is facilitated.

Preferably, after axially and rotationally displacing the piston rod assembly 32 in the dose delivery direction the interaction member 23 may abut the blocking means 19 of the adjacent dose section as described above. Alternatively, the piston rod assembly 32 may have been displaced in the dose delivery direction such that the interaction member 23 is arranged at a distance with respect to the blocking means 19 of the adjacent dose section.

Figure 6A:
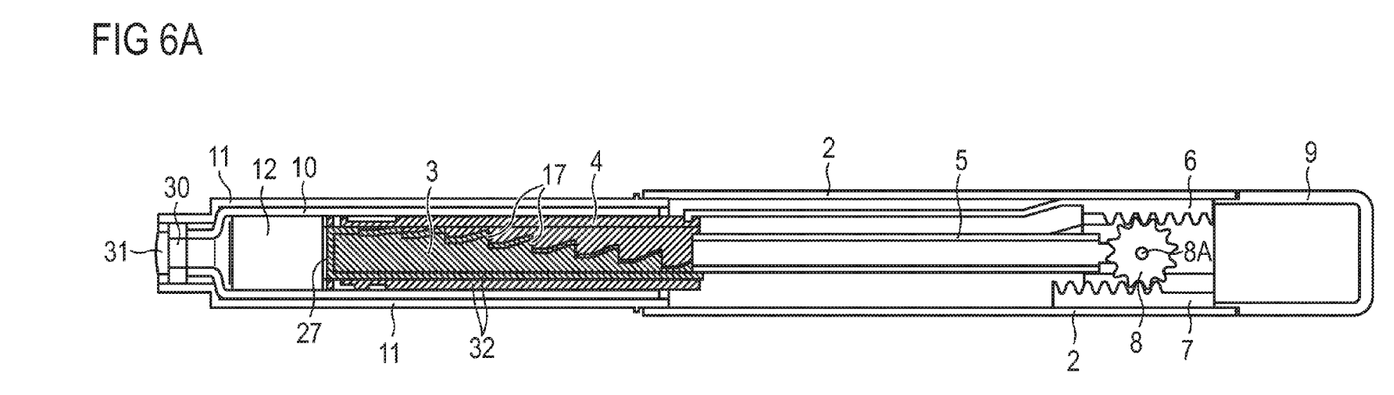
Figure 6B:
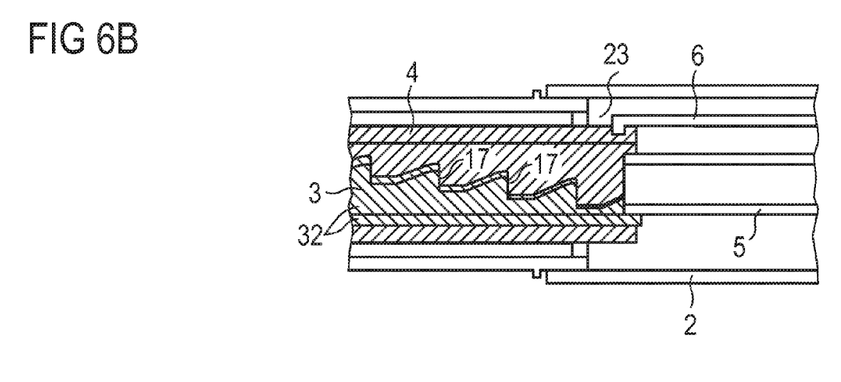

FIG. 6A and FIG. 6B schematically show the drug delivery device of FIG. 1 after delivery of the last dose.

From delivery of the first dose of the drug 24 (see FIG. 1), when the piston rod assembly 32 is in the axial starting position, to delivery of the last dose (FIG. 6), the piston rod assembly 32 may have been rotated by 360 degrees or less with respect to the housing 2. Preferably, the piston rod assembly 32 has been rotated by less than 180 degrees with respect to the housing 2. The rotation angle from delivery of the first dose to delivery of the last dose corresponds to the angular extension of the delivery section 18A as seen over its total axial extension.

After having dispensed the last dose, the drive feature 15 cooperates with the interaction surface 17 arranged closest to the proximal end of the piston rod 3 (FIG. 6). The interaction member 23 interacts with the dose section being arranged closest to the proximal end of the piston rod sleeve 4. Now, the device 1 may be reset for dispensing a plurality of a doses of a drug held in a replacement cartridge. In the following, operation of resetting the drug delivery device 1 may be described.

Firstly, the cartridge holder 11 is unsecured from the housing 2. The empty cartridge 10 is removed from the cartridge holder 11. The piston rod assembly 32 may now be set back to its axial starting position. The axial starting position of the piston rod assembly 32 may be 180 degrees rotated about the main longitudinal axis 28 of the piston rod assembly 32 with respect to the previous starting position of the piston rod assembly 32 as described above. Afterwards, the replacement cartridge is introduced into the cartridge holder 11. The cartridge holder 11 holding the replacement cartridge is finally secured to the housing 11.

For resetting the drug delivery device 1, in particular for resetting the piston rod assembly 32 back to its axial starting position, the interaction member 23, which is still arranged to cooperate with the delivery section 18A after having dispensed the last dose, has to be put into cooperation with the reset section 18B. For this purpose, the piston rod assembly 32 is rotated in the same direction as during dose delivery with respect to the housing 2. The piston rod assembly 32 may be rotated such that the interaction member 23 mechanically cooperates with the connection region 25 (see FIGS. 2 and 3). Thereby, the connection region 25 is passed over the interaction member 23. The interaction member 23 interacts with the section separator 29. The section separator 29 may be a step, for example.

Once the section separator 29 has been passed over interaction member 23, the section separator 29 may block rotation of the piston rod assembly 32 in the opposite direction with respect to the housing 2 which would put the interaction member 23 back into interaction with the delivery section 18A. Hence, the section separator 29 provides for a uni-directional coupling between the connection region 25 and the interaction member 23. When the section separator 29 is passed over interaction member 23 the user will be given an audible and/or tactile feedback which may indicate that the device 1 is ready for a reset movement of the piston rod assembly 32.

Aside from the angularly extending connection region 25 between delivery section 18A and reset section 18B a transition between the delivery section 18A and the reset section 18B in the angular direction may be prevented due to mechanical cooperation of the interaction member 23 and the sidewall of the delivery section 18A. Hence, a reset of the device 1 may be prevented unless a last dose held in the cartridge 10 has been delivered and the interaction member 23 is brought into interaction with the reset section 18B via the connection region 25. Accordingly, after delivery of the last dose a further dose setting and dose delivery operation may be prevented unless reset of the device 1 is completed, i.e. unless the piston rod assembly 32 is displaced along the reset section 18B to another connection region 25 and rotated in the same direction as during dose delivery for bringing the interaction member 23 into mechanical cooperation with the delivery section 18A or another delivery section via the connection region 25.

Rotation of the piston rod assembly 32 in the same direction as during dose delivery with respect to the housing 2 for resetting the device 1 may help to put the interaction surfaces 17 into a position such that mechanical cooperation of the interaction surfaces 17 and the drive feature 15 may be prevented when resetting the piston rod assembly 32 back to its axial starting position. Due to rotation of the piston rod assembly 32 the interaction surfaces 17 may be angularly displaced with respect to the drive feature 15. Hence, the interaction surfaces 17 may pass the axial position of the drive features 15 with an angular offset. The drive feature 15 may be arranged in an axial channel free of interaction surfaces 17.

Once the piston rod assembly 32 has been rotated such that the interaction member 23 mechanically cooperates with the reset section 18B the piston rod assembly 32 may be axially displaced along the reset section 18B towards the axial starting position (see arrow 26 in FIG. 3).

The reset section 18B may be free of blocking means 19 as described in connection with FIGS. 2 and 3. Preferably, the reset section 18B is angularly offset from the delivery section 18A such that the blocking means 19 of the delivery section 18A may pass the axial position of the interaction member 23 with an angular offset when the interaction member 23 cooperates with the reset section 18B. Hence, when axially displacing the piston rod assembly 32 towards the axial starting position, the blocking means 19 may pass the axial position of the interaction member 23 without mechanical interaction with the interaction member 23. This may enable displacement of the piston rod assembly 32 axially alongside the delivery section 18A. In this way, a resettable drug delivery device is achieved.

The reset track 18B may be arranged such that the user may push the piston rod assembly 32 towards the axial starting position with the replacement cartridge being secured in the cartridge holder 11 or separately.

The reset track 18B may be ramp-shaped or may comprise a ramp, for example. The ramp may rise in the distal direction. When the piston rod assembly 32 has been moved along the reset track 18B into the axial starting position, the piston rod assembly 32, may be rotatable with respect to the housing 2. The piston rod assembly 32 may be rotated in the same direction as during dose delivery to put the interaction member 23 in mechanical cooperation with the delivery section 18A or an other delivery section 18A. This rotation of the piston rod assembly 32 that engages the interaction member 23 with delivery section 18A may be achieved by cooperation between the features of the piston rod assembly 3,4 and features of the cartridge holder 11, occurring when the cartridge holder 11 is re-attached, e.g. by means of a thread, to the housing 2. Previously, rotation with respect to the housing 2 may have been prevented by mechanical cooperation of the interaction member 23 and a sidewall of the reset section 18A.

For rotating the piston rod assembly 32 the interaction member 23 may cooperate with connection region 25. Thereby, the section separator 29, which is arranged in said connection region 25, may be passed over the interaction member 23. The interaction member 23 may click over the section separator 29. This may give the user an audible feedback that the device 1 has been correctly reset. As described previously, the section separator 29 may serve as non-return feature. The section separator 29 may again block rotation of the piston rod assembly 32 in the direction opposite to the one during dose delivery with respect to the housing 2 which would put the interaction member 23 back into interaction with the reset section 18B.

Rotation of the piston rod assembly 32 with respect to the housing 2 for putting the interaction member 23 in cooperation with the delivery section 18A or with another delivery section 18A may also serve for putting the interaction surfaces 17 into an angular position such that mechanical cooperation of the interaction surfaces 17 and the drive feature 15 is enabled for delivering a priming dose or a next first dose of the drug 24, i.e. the first dose from the replacement cartridge.

The drive mechanism described above provides for a low number of components. Hence, the drive mechanism may be particularly attractive for cost sensitive device applications. Additionally, the device 1 and, in particular the drive mechanism, may be less prone to errors in manufacture and assembly due to the low number of components. The device 1 may provide simple user operation.

The device 1 may, for example, be configured for setting and delivering doses of 30 IU or greater, for example a dose of 50 IU or greater, thereby providing high dose accuracy. Alternatively, the device 1 may be designed for doses of 5 IU or less, preferably 1 IU or less, or any dose in-between while having high dose accuracy.

The device 1 may be especially suited to dispense a plurality of pre-set doses of the drug 24 held in the cartridge 10.

Further features and refinements become apparent from the following description of the exemplary embodiments in connection with the accompanying figures.

REFERENCE NUMERALS

1 Drug delivery device
2 Housing
3 Piston rod
4 Piston rod sleeve
5 Drive member
6 First rack
7 Second rack
8 Gear
8A Axle
9 Dose member
10 Cartridge
11 Cartridge Holder
12 Piston
13 Distal end 14 Proximal end
15 Drive feature
16 Engaging means
17 Interaction surface
17A Interaction surface
17B Interaction surface
17C Interaction surface
18 Guide track
18A Delivery section
18B Reset section
19 Blocking means
20 Arrow
21 Arrow
22 Stop member
23 Interaction member
24 Drug
25 Connection region
26 Arrow
27 Bearing member
28 Main longitudinal axis of piston rod assembly
29 Section separator
30 Ramp
31 Ramp
32 Piston rod assembly

The invention claimed is:

1. A resettable drive mechanism for a drug delivery device comprising a piston rod assembly, the piston rod assembly comprising:
  a guide track running along the piston rod assembly, the guide track comprising at least one delivery section and at least one reset section, the at least one reset section being arranged to continue the at least one delivery section, the at least one delivery section comprising at least one blocking means, and
  an interaction member, the interaction member being configured to cooperate with the guide track,
  wherein, for delivering a dose of a drug,
  (i) the piston rod assembly is axially displaceable in a dose delivery direction away from an axial starting position,
  (ii) the interaction member cooperates with the at least one delivery section, and
  (iii) the blocking means beginning at a position proximal to the interaction member and moving distally thereby passing the interaction member to a position distal of the interaction member when the piston rod assembly is displaced in the dose delivery direction,
  wherein axial displacement of the piston rod assembly towards the axial starting position is prevented by mechanical interaction of the blocking means and the interaction member when the interaction member cooperates with the at least one delivery section, and
  wherein, for resetting the drug delivery device,
  (i) the interaction member is configured to cooperate with the at least one reset section,
  (ii) the piston rod assembly is axially displaced towards the axial starting position, and
  (iii) the blocking means is offset from the interaction member and passing the interaction member when the piston rod assembly is axially displaced towards the axial starting position.

2. The resettable drive mechanism of claim 1, wherein the at least one reset section is arranged to form a continuous circuit with the at least one delivery section.

3. The resettable drive mechanism of claim 1, wherein, when the interaction member cooperates with the at least one reset section, the blocking means is angularly offset from the interaction member.

4. The resettable drive mechanism according to claim 1, wherein the at least one reset section extends axially along the at least one delivery section.

5. The resettable drive mechanism according to claim 1, wherein the at least one reset section is angularly offset with respect to the at least one delivery section and the angular offset between the at least one reset section and the at least one delivery section decreases in the axial direction away from the axial starting position.

6. The resettable drive mechanism according to claim 1, wherein the at least one delivery section is connected to the at least one reset section via an angularly extending connection region of the guide track.

7. The resettable drive mechanism of claim 6, wherein, for resetting the drive mechanism, the piston rod assembly is rotatable such that the connection region passes the interaction member and the interaction member is put into mechanical cooperation with the at least one reset section.

8. The resettable drive mechanism according to claim 7, wherein a section separator is arranged in the connection region, the section separator blocking rotation of the piston rod assembly in a direction which would put the interaction member back into interaction with the at least one delivery section via the connection region.

9. The resettable drive mechanism of claim 6, wherein a transition from the at least one delivery section into the at least one reset section is permitted only via the connection region.

10. The resettable drive mechanism according to claim 1, wherein the at least one delivery section extends obliquely with respect to the main longitudinal axis of the piston rod assembly and the at least one reset section extends less obliquely with respect to the main longitudinal axis of the piston rod assembly than the at least one delivery section.

11. The resettable drive mechanism according to claim 1, wherein the at least one delivery section and the interaction member define a rotation angle by which the piston rod assembly is rotated by mechanical interaction of the interaction member and the at least one delivery section when the piston rod assembly is axially displaced for delivering a dose.

12. The resettable drive mechanism according to claim 1, wherein, when the piston rod assembly has been moved back into the axial starting position, the piston rod assembly is rotatable to put the interaction member in mechanical cooperation with the at least one delivery section or an other delivery section.

13. The resettable drive mechanism according to claim 1, wherein the drive mechanism comprises a drive member, the drive member being configured to drive the axial displacement of the piston rod assembly in the dose delivery direction by mechanical interaction of an interaction surface of the piston rod assembly with a drive feature of the drive member, and wherein, for resetting the drug delivery device, the piston rod assembly is configured to be rotatable such that the interaction surface is angularly displaced with respect to the drive feature such that the interaction surface may pass the axial position of the drive feature with an angular offset.

14. The resettable drive mechanism according to claim 13, wherein the guide track is provided at an outer surface of the piston rod assembly and the interaction surface is provided at an inner surface of the piston rod assembly.

15. The resettable drive mechanism according to claim 1, wherein the at least one delivery section comprises a plurality of dose sections with two adjacent dose sections being separated by the blocking means.

16. The resettable drive mechanism according to claim 1, wherein the at least one delivery section extends in the angular direction by less than 360 degree over its total axial extension.

* * * * *